United States Patent [19]

Sakoda et al.

[11] Patent Number: 5,439,866
[45] Date of Patent: Aug. 8, 1995

[54] SILVER-CONTAINING TOBERMORITE

[75] Inventors: Naokazu Sakoda; Kouju Sugiyama, both of Osaka, Japan

[73] Assignee: Rengo Co., Ltd., Osaka, Japan

[21] Appl. No.: 108,574

[22] PCT Filed: Mar. 4, 1993

[86] PCT No.: PCT/JP93/00284
§ 371 Date: Nov. 1, 1993
§ 102(e) Date: Nov. 1, 1993

[87] PCT Pub. No.: WO93/17964
PCT Pub. Date: Sep. 16, 1993

[30] Foreign Application Priority Data

Mar. 6, 1992 [JP] Japan ................... 4-084795

[51] Int. Cl.⁶ .................... B01J 20/04; B01J 20/12
[52] U.S. Cl. .................... 502/407; 502/410
[58] Field of Search .................... 502/407, 410

[56] References Cited

FOREIGN PATENT DOCUMENTS

| | | | |
|---|---|---|---|
| 0147287 | 8/1985 | Japan | 502/410 |
| 3156540 | 6/1988 | Japan | 502/407 |
| 2031393 | 4/1980 | United Kingdom | 502/407 |

*Primary Examiner*—Asok Pal
*Attorney, Agent, or Firm*—Nikaido, Marmelstein, Murray & Oram

[57] ABSTRACT

A novel silver-containing tobermorite usable in place of silver-, copper- or zing-incorporating zeolites and having ethylene-adsorbing ability and antibacterial properties. Stated more particularly, a silver-containing tobermorite having a composition of $[Ca_{5-Y/2}Ag_{Y+Z}M_{x-z}(Si_{6-x}Al_xO_{18}H_2)].4H_2O$, $0 \leq X \leq 1$, $0.001 \leq Y \leq 2$, $0 \leq Z \leq 0.1$, M is a monovalent cation] and prepared from a tobermorite $[Ca_5M_x(Si_{6-x}Al_xO_{18}H_2).4H_2O$, $0 \leq X \leq 1$, M is as defined above] by exchanging $Ca^{2+}$, or $Ca^{2+}$ and a monovalent cation which are interlayer ions of the tobermorite for silver ion. The silver-containing tobermorite is excellent in heat resistance, water resistance and mechanical strength, and also outstanding in ethylene-adsorbing ability and antibacterial properties.

1 Claim, 9 Drawing Sheets

SILVER-CONTAINING TOBERMORITE

TECHNICAL FIELD

The present invention relates to a novel tobermorite, and more particularly to a novel tobermorite carrying silver ions between its layers, excellent in resistance to heat and water and in mechanical strength and having ethylene-adsorbing ability and anti-bacterial properties.

BACKGROUND ART

Zeolites are well known as typical examples of inorganic ion exchangers. Zeolites are capable of supporting various metals through cation exchange of $Na+$ ions or $Ca^{2+}$ ions in the interior of their crystals for metal cations in an aqueous solution. Further zeolites have excellent characteristics with respect to specific surface area, heat resistance, water resistance, mechanical strength, etc. and are therefore widely used as gas adsorbing and separating agents, agents for treating waste water containing heavy metals, ion fixing agents and carriers for metal catalysts.

Zeolites are crystalline substances consisting primarily of $SiO_2$ and $Al_2O_3$, and the crystals thereof have three-dimensional structure and have regular minute pores. The composition is expressed generally by $(M_2, M')O \cdot Al_2O_3 \cdot mSiO_2 \cdot nH_2O$ wherein M and M' are monovalent and bivalent metal ions, respectively, m is the coefficient of silica, and n is the coefficient of crystal water. Zeolites include the faujasite group (sodalite group), chabazite group and mordenite group which are different in the structure of crystals. The cations present in the voids or channels of zeolites can be exchanged for other metal ions, so that zeolites are utilized for softening hard water and separating off metal ions. When the alkali metal of zeolites is exchanged for bivalent or trivalent metal ions or hydrogen ions, the zeolite forms a strong solid acid, which is useful as an excellent catalyst for cracking petroleum and various carbonium ion reactions. Zeolites carrying silver, copper, zinc or the like supported thereon are kneaded with polymers to prepare antibacterial wrapping materials for preventing deterioration for use in the field of foods. Especially, the silver-incorporating zeolite is also excellent in ethylene-adsorbing ability and is therefore valuable for use.

However, the zeolites incorporating silver, copper or zinc fail to fulfill the requirement of being inexpensive which is characteristic of inorganic materials because of material costs and complex manufacturing process, and are very expensive materials.

Accordingly, the object to be achieved by the present invention is to develop a novel inorganic material which is usable in place of the silver-, copper- or zinc-incorporating zeolites and which has ethylene-adsorbing ability and antibacterial activity.

This object is fulfilled by exchanging $Ca^{2+}$ ions, of these ions and monovalent cations, such as $Na+$ ions, which are present between the layers of a tobermorite for silver ions into the tobermorite although this has never been practiced in the past.

A description will be given with reference to $Na+$ ion which is typical of monovalent cations.

We have directed attention to tobermorites which are fibrous layered compounds heretofore widely used as lightweight heat-insulating materials and noncombustible building materials because of their resistance to a high temperature of 650° C. and excellent heat-insulating properties, and conceived the entirely novel idea that the $Ca^{2+}$ ions, or these ions and $Na+$ ions which are present between the layers of the mineral can presumably be exchanged for silver ions by cation exchange. We have carried out intensive research based on this idea and consequently succeeded for the first time in the cation exchange of $Ca^{2+}$ ions, or these ions and $Na+$ ions, which are present between the layers of a tobermorite, for silver ions. We have further found that this novel substance has ability to adsorb ethylene and antibacterial activity.

Disclosure of the Invention

Tobermorite, which is a mineral rarely occurring naturally, is an important component mineral of ALC (Autoclaved Lightweight Concrete) and is a typical fibrous hydrate having a relatively large specific surface area of 50 to 90 m²/g.

The composition of pure tobermorite is expressed by $5CaO \cdot 6SiO_2 \cdot 5H_2O$, and the rational formula thereof is $Ca_5(Si_6O_{18}H_2) \cdot 4H_2O$. The mineral is of rhombic system (a=11.3 angstroms, b=7.3 angstroms, c=22.6 angstroms) and is termed also 11-angstrom tobermorite.

Tobermorite has a layered structure closely resembling that of kaolinite which is a clay mineral. One of the layers is a $[Ca_4/Si_3O_9H)_2]^{2-}$ layer in which a Ca—O layer in the center is sandwiched between groups of $SiO_3$ chains. The remaining $Ca^{2+}$ ion and four molecules of $H_2O$ are filled in voids (interlayer spaces) formed by torsion of $SiO_3$ chains, and such $Ca^{2+}$ ions are exchanged for silver ions according to the present invention.

Tobermorite is readily obtained by subjecting a mixture of CaO and quartz (or kieselguhr) with a $CaO/SiO_2$ ration of 1.0 to a hydrothermal reaction at 180° C. in an autoclave. In the initial stage of the reaction, Ca-rich C-S-H phases (comprising various calcium silicate compounds) are formed, but as $SiO_2$ becomes progressively dissolved, the $CaO/SiO_2$ ratio of the reaction product decreases to result in gradual crystallization of 11-angstrom tobermorite.

The above-mentioned conventional tobermorites which are usable as lightweight heat-insulating materials and the like can of course be used as the starting material tobermorite according to the present invention.

It is also possible to synthesize a tobermorite which has incorporated in its structure up to 16.7 mole % (Al/Si+Al) of Al relative to Si and a monovalent cation by a reaction for substituting Al for Si. This tobermorite is generally termed Al-substituted tobermorite. It is generally known that in the synthesis of tobermorite, presence of $Na^+$, $K^+$ of like alkali metal ions results in promoted crystallization, and also that these alkali metal ions themselves participate in the cation exchange reaction as interlayer ions.

For example, with an Al-substituted tobermorite containing $Na^+$ ions as the ion M in the tobermorites of the invention to be described later, such $Na+$ ions become electively exchanged for other monovalent cations ($K^+$, $Cs^+$, $NH^{4+}$, etc.), and moreover, a larger amount of cations are exchanged than in the case of pure tobermorite.

This Al-substituted tobermorite is also usable as the starting material tobermorite according to the invention. In fact, the tobermorite used in the examples of the invention given later is an Al-substituted tobermorite which contains 9.2 mole % of substituted Al for Si, and Na+ ions and H+ ions as ion M.

Thus, the tobermorites to be used in the present invention are those represented by [$Ca_5M_X(Si_{6-X}Al_XO_{18}H_2)\cdot 4H_2O$, $0 \leq X \leq 1$, M is a monovalent cation]. Examples of useful monovalent cations can be $H^+$, $Li^+$, $Na^+$, $K^+$, $Rb^+$, $Cs^+$ and $NH_4^+$. Several kinds of such monovalent cations may be present in the Al-substituted tobermorite at the same time without any problem.

The crystal water of pure tobermorite comprises four molecules of interlayer crystal water and one molecule of intramolecular crystal water as is known from the rational formula $Ca_5(Si_6O_{18}H_2)\cdot 4H_2O$. Heating the tobermorite removes the interlayer crystal water at 150° to 550° C. and the intramolecular crystal water at around 650° C., and breaks down the tobermorite structure at about 800° C. to convert the tobermorite to wollastonite ($\beta$-$CaSiO_3$). Al-substituted tobermorites also exhibit the same dehydration behavior.

The silver-containing tobermorite of the present invention is obtained by immersing dry fine powder of the above-mentioned tobermorite in one of aqueous solutions of silver nitrate having varying conentrations at room temperature for several hours. The powder is usually about 0.5 to about 20 micrometers in particle size.

In considering the reaction between tobermorites and silver ions, the cation exchange capacity of the tobermorite can be expressed by the sum of twice the mole number of $Ca^{2+}$ ions and the mole number of $Na^+$ ions which are present between the layers of 1.0 g of tobermorite. For example, 1.0 g of pure tobermorite (730.90 in molecular weight) contains 1.37 mmoles of $Ca^{2+}$ ions between the layers thereof, so that the silver ion exchange capacity thereof is 2.74 mmoles/g. On the other hand, 1.0 g of the Al-substituted tobermorite (739.42 in molecular weight) used in the examples given later contains 1.35 mmoles of $Ca^{2+}$ ions and 0.53 mmoles of $Na^+$ ions between the layers thereof, so that the cation exchange capacity thereof is 3.23 mmoles/g. As will be described later with reference to Example 2, however, we found that when subjected to a cation exchange reaction in an aqueous solution of silver nitrate of high concentration, 1.0 g of the Al-substituted tobermorite was made to support only 2.80 mmoles of silver ions which was below the cation exchange capacity, and that the amounts of $Ca^{2+}$ ions and $Na^+$ ions released into the aqueous solution by the reaction approximately corresponded to 100% of the amount of $Ca^{2+}$ ions and 10% of the amount of $Na^+$ ions present as interlayer ions in the Al-substituted tobermorite.

This reveals that in the reaction of the Al-substituted tobermorite with silver ions, silver ions, although monovalent cations, are not exchanged for the interlayer $Na^+$ ions selectively but are selectively exchanged for the interlayer $Ca^{2+}$ ions unlike the case wherein the interlayer $Na^+$ ions of the Al-substirated tobermorite are selectively reacted with other monovalent cations such as $K^+$ ions $Cs^+$ ions.

Thus, the maximum amount of ion exchange of the Al-substituted tobermorite for silver ions is 2.80 mmoles/g, such that the silver substitution reaction, even if conducted at a higher temperature, higher pressure and higher concentration, merely results in a breakdown of the crystal structure of tobermorite or formation of by-products, failing to cause the tobermorite to support a larger amount of silver ions. This is also true of pure tobermorite. Although all the interlayer $Ca^{2+}$ ions present between the layers thereof can be exchanged for silver ions, it is impossible to cause this tobermorite to support silver ions in an amount larger than its cation exchange capacity, i.e., more than 2.74 mmoles/g.

Stated conversely, this means that the amount of silver ions to be supported by the silver-containing tobermorite of the present invention is controllable as desired merely by varying the concentration of the aqueous silver nitrate solution for use in the cation exchange method at room temperature without breaking the layered structure which is characteristic thereof.

Although the method of cation exchange according to the invention is not limited in any way, the following conditions are usually used.

1) Use of an aqueous solution, such as an aqueous solution of silver nitrate, in which silver ions are completely dissociated. If otherwise, not only reduced reactivity will result but also impurities become mixed with the product.
2) The pH value of the solution to be reacted is usually 3 to 10. If the value is less than 3, the solution dissolves tobermorite, whereas if it is higher than 10, silver ions precipitate in the form of a basic salt.
3) The reaction temperature is usually 0° to 100° C. If the temperature is lower than 0° C., the solution freezes without assuming the form of an aqueous silver ion solution. Even when the aqueous solution then remains as such, for example, because of a high silver ion concentration, the reaction takes place very moderately and is not suited to cation exchange. Conversely if the temperature is higher than 100° C., the reactor fails to maintain the solution at a constant silver ion concentration owing to vigorous evaporation of water when it is an open system or is likely to permit breakage of the structure of tobermorite when it is a closed system.

Typical of such conditions are about 2.5 g in the amount (weight) of tobermorite, 5.0 in pH, 25° C. in liquid temperature, 10.0 mmoles per liter (1.0) in the silver ion concentration of the solution to be reacted, and batchwise reaction for 24 hours.

Although the greatest feature of the present invention is that the interlayer $Ca^{2+}$ ions, or these ions and $Na^+$ ions present between the layer Si of a tobermorite are exchanged for silver ions, the interlayer $Ca^{2+}$ ions present in the layers of the tobermorite may further be exchanged for silver ions insofar as the crystal structure of the tobermorite is not changed.

The novel substance of the present invention, i.e., silver-containing tobermorite, exhibits satisfactory ethylene adsorbing ability and antibacterial activity even when containing only 0.04 mmole/g of silver ions as will be described with reference to Examples. The silver ions once substituted for $Ca^{2+}$ ions in the tobermorite by cation exchange remain therein almost without dissolving out into the aqueous phase even when repeatedly washed with distilled water. Even if silver ions dissolve out, this is limited only to cases of large amounts of supported silver, and the amount released is of the order of p.p.b. within a permissible range.

The tobermorite as the material for the silver-containing tobermorite originally has heat resistance, water resistance and great mechanical strength, so that the silver-containing tobermorite also has similar physical properties. For example, TG-DTA curves representing thermal properties indicate that the silver-containing tobermorite slightly differs from the material tobermorite in the dehydration behavior of the interlayer crystal water at around 300° C. but is exactly the same as the material in losing the intramolecular crystal water at 650° C. and in changing into wollastonite ($\beta$-CaSiO$_3$) at about 800° C. and further retains the original heat resistance of tobermorite.

Further when observed under an electron microscope, the silver-containing tobermorite is found to retain the same fibrous crystal form as the tobermorite before incorporating silver, so that the silver-containing tobemorite is usable in all technical field wherein tobermorites are utilized. Moreover, the silver-containing tobermorite has ethylene adsorbing ability and antibacterial activities and is therefore usable in new fields as an agent for enabling vegetables and fruits to retain freshness and as a deterioration preventing agent for many foods. Incidentally, the conventional known tobermorites supporting no silver ions exhibit almost neither of the contemplated ethylene adsorbing ability and antibacterial activities.

Furthermore, the tobermorite serving as the material for the silver-containing tobermorite consists primarily of CaO and quartz (SiO$_2$) which are contained in large amounts in soil, so that when discarded after use, the silver-containing tobermorite gradually decomposes in soil and is converted again into soil components. Thus, it is friendly and safe to the earth.

BRIEF DESCRIPTION OF THE DRAWINGS

FIG. 2 is a graph showing an X-ray diffraction pattern of TO;

FIG. 4 is a graph showing an IR pattern of TO;

FIG. 6 is a graph showing an electron photomicrograph of TO;

FIG. 8 is a graph showing TG-DTA curves of TO;

Best Mode of Carrying Out The Invention

The present invention will be described in greater detail with reference to the following examples and experimental examples.

Example 1

The tobermorite used in the following examples as a material for novel substances of the invention was prepared from CaO obtained by calcining calcium oxide, a reagent of first grade, at 1000° C. for 3 hours, amorphous silica (SiO$_2$ gel), NaOH (reagent of special grade) and Al(NO$_3$)$_3$ · 9H$_2$O by charging these starting materials into an autoclave along with distilled water so as to give a reaction mole ratio Ca:Si:Na:Al of 5:5.5:0.5:0.5 and reacting the materials at 175° C. for 96 hours.

The slurry resulting from the reaction was then washed with distilled water, and the solids were separated off after the supernatant reduced to a pH of not higher than 8 and were dried at 105° C. When the starting material CaO was used in an amount of 1.0 kg, about 2630 g of tobermorite was obtained. Next, the sample was pulverized to 200 to 400 mesh for use in the examples. Table 1 shows the composition, mean particle size and specific surface area of the tobermorite (hereinafter referred to as "TO") serving as the material for novel substances of the invention, i.e., silver-containing tobermorites.

TABLE 1

| Sample | Composition | Particle size ($\mu$) | Specific surface area (m$^2$/g) |
| --- | --- | --- | --- |
| Tobermorite (T$_0$) | Ca$_5$Na$_{0.39}$H$_{0.16}$—(Si$_{5.45}$Al$_{0.55}$O$_{18}$H$_2$).4H$_2$O | Av. 5.7 | 57.5 |

In the present example, the tobermorite (TO) thus prepared and an aqueous solution of silver nitrate having a concentration of 10.0 mM were used to check the characteristics of cation exchange between the exchangeable interlayer cations of the tobermorite, i.e., Ca$^{2+}$ and Na$^+$ ions, and the silver ions in the aqueous solution. The present example afforded for the first time the novel substance of the invention, silver-containing tobermorite.

A 2.54 g quantity of the dry fine tobermorite powder (containing about 3.38 mmoles of Ca$^{2+}$ ions and about 1.32 mmoles of Na$^+$ ions, exchangeable interlayer ions, which are theoretically exchangeable for 8.08 mmoles of silver ions) was admixed with 1.0 liter of 10.0 mM aqueous silver nitrate solution and reacted therewith with stirring in a water bath having a constant temperature of 25° C. To prevent formation of carbonate, oxide and like by-products, the solution was deaerated, and the air to be in contact with the solution was replaced by nitrogen. The resulting reaction mixture was filtered by suction using a Buchner funnel to separate off a solid portion from a liquid.

Figure 1:
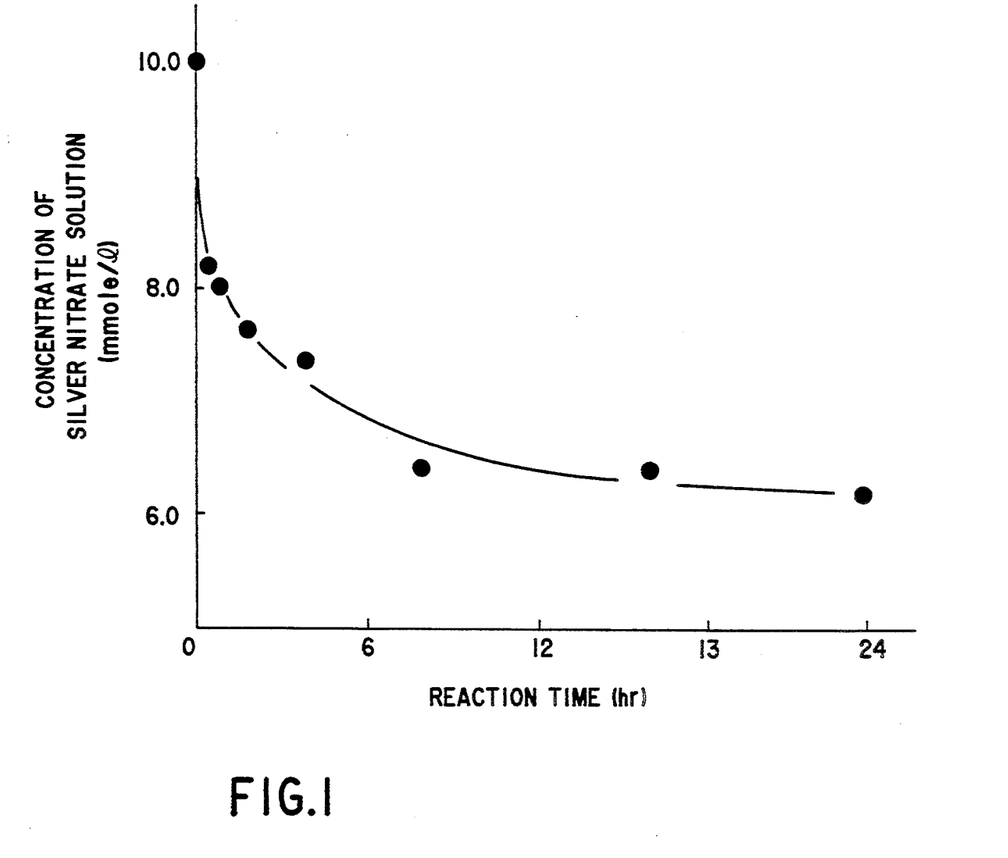
FIG. 1 is a graph showing characteristics of cation exchange between TO and silver ions.

The silver, Ca$^{2+}$ and Na$^+$ ion concentrations of the liquid were determined at a predetermined time interval by the Volhard method, EDTA chelate titration method and atomic absorption method, respectively. FIG. 1 and Table 2 show the results. In FIG. 1, the solid dots represent silver ions.

Figure 2:
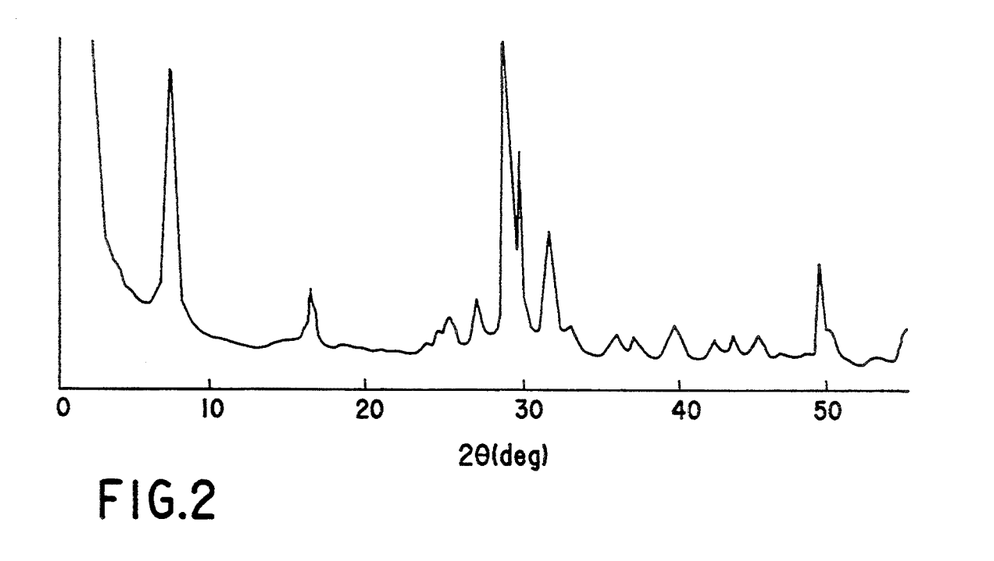
Figure 3:
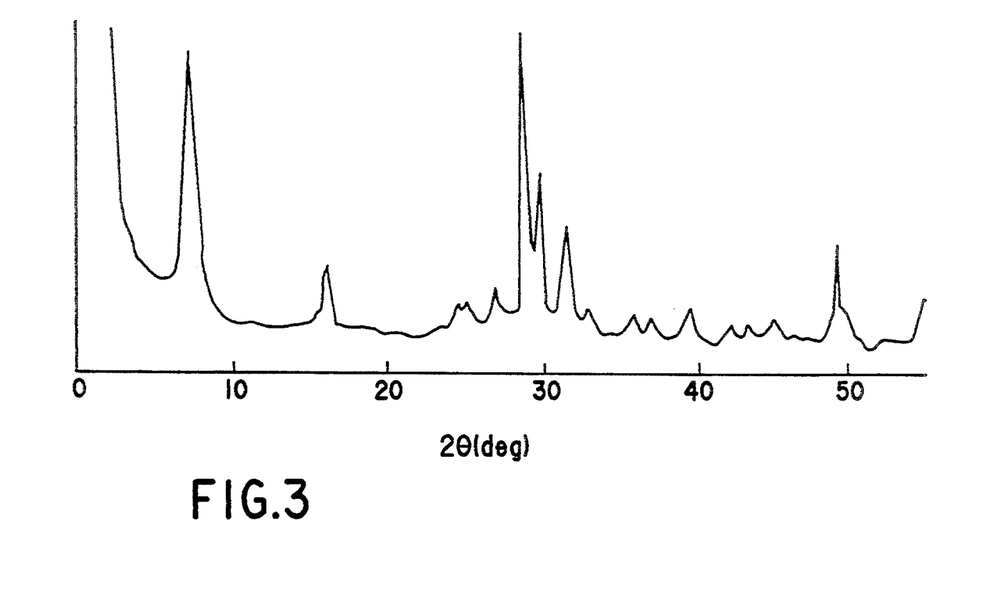
FIG. 3 is a graph showing an X-ray diffraction pattern of T1 to T5.

The solid portion was washed with 2.0 liters of distilled water and thereafter dried in a vaccum at room temperature, and the powder was checked for the presence of by-products by the X-ray diffraction method. FIGS. 2 and 3 show the result. FIG. 2 shows the result obtained with TO, and FIG. 3 those obtained with T1 to T5. Referred to as T1 to T5 are the novel substances of the invention, silver-containing tobermorites, prepared in Example 3 to follow.

TABLE 2

| Reaction time (hr) | 0 | 1 | 2 | 4 | 8 | 16 | 24 |
| --- | --- | --- | --- | --- | --- | --- | --- |
| Ag$^+$ ion conc. (mmole/l) | 10.0 | 7.88 | 7.51 | 7.24 | 6.31 | 6.29 | 6.07 |
| Ca$^{2+}$ ion conc. (mmole/l) | 0 | 1.10 | 1.24 | 1.40 | 1.75 | 1.87 | 2.09 |

TABLE 2-continued

| Reaction time (hr) | 0 | 1 | 2 | 4 | 8 | 16 | 24 |
|---|---|---|---|---|---|---|---|
| $Na^+$ ion conc. (mmole/l) | 0 | 0.01 | 0.02 | 0.02 | 0.03 | 0.03 | 0.03 |
| Amount of $Ag^+$ ions removed (mmole) | 0 | 2.12 | 2.49 | 2.76 | 3.69 | 3.71 | 3.93 |
| $Ag^+$ ion removal ratio (%) | 0 | 21.2 | 24.9 | 27.6 | 36.9 | 37.1 | 39.3 |
| Reaction mole ratio ($Ca^{2+}/Ag^+$) | 0 | 0.56 | 0.50 | 0.50 | 0.48 | 0.50 | 0.53 |

Table 2 and FIG. 1 reveal that the concentration of silver ions in the aqueous solution gradually decreased with time and leveled ore to a steady state in 24 hours. The concentrations of silver ions, $Ca^{2+}$ ions and $Na^+$ ions in the aqueous solution at this time were 6.07 mM, 2.09 mM and 0.03 mM, respectively, and the amount of $Ca^{2+}$ ions and $Na^+$ ions released into the aqueous solution was about 50% (2.12 mmoles) of the decrease in the amount of silver ions (3.93 mmoles). The amount of released $Ca^{2+}$ included in the above-mentioned amount of released ions was about 62% of all interlayer $Ca^{2+}$ ions, while the corresponding value of $Na^+$ ions was about 2.2%.

This indicates that the reaction between the interlayer ions in the tobermorite and silver ions is a cation exchange reaction which is 2:1 in reaction mole ratio ($Ag^+/Ca^{2+} + Na^+$), and that silver ions in the aqueous solution selectively react with $Ca^{2+}$ ions although failing to react with $Na^+$ ions noticeably.

The cation exchange reaction resulting in the introduction of silver ions produced no change in the powder X-day diffraction pattern of the tobermorite sample, and none of by-products such as carbonate, oxide, etc. were detectable from the reaction product.

This demonstrates that the substance obtained in the present example is a novel substance having silver ions as interlayer ions of the tobermorite.

Figure 4:
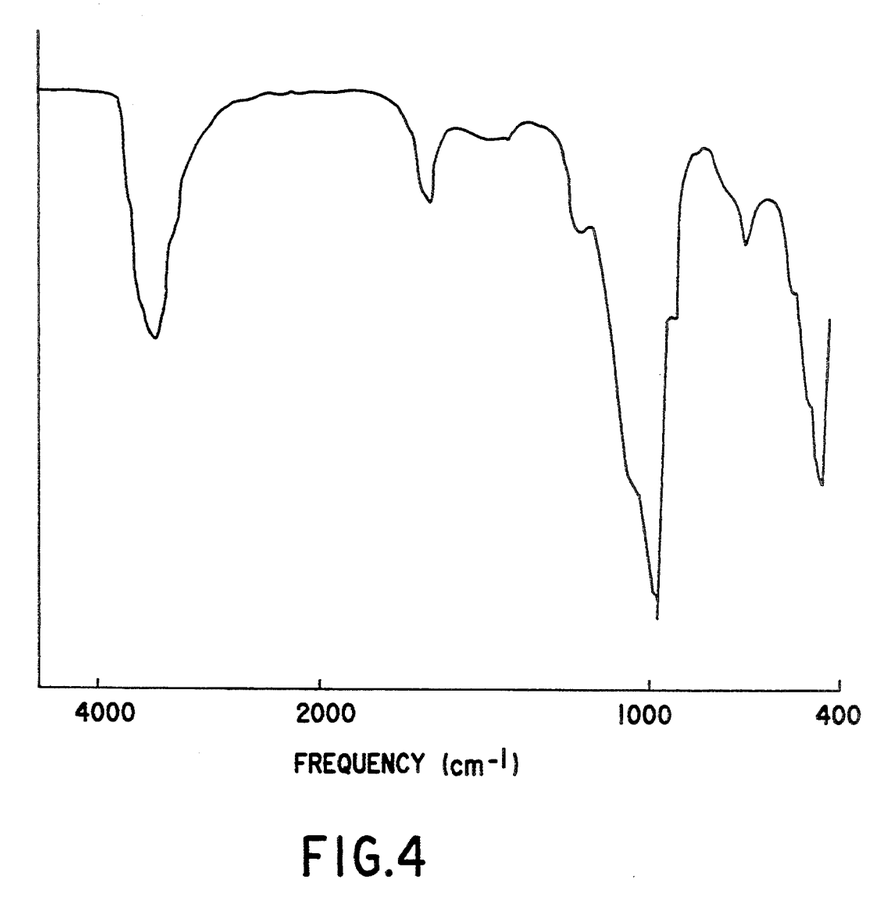
Figure 5:
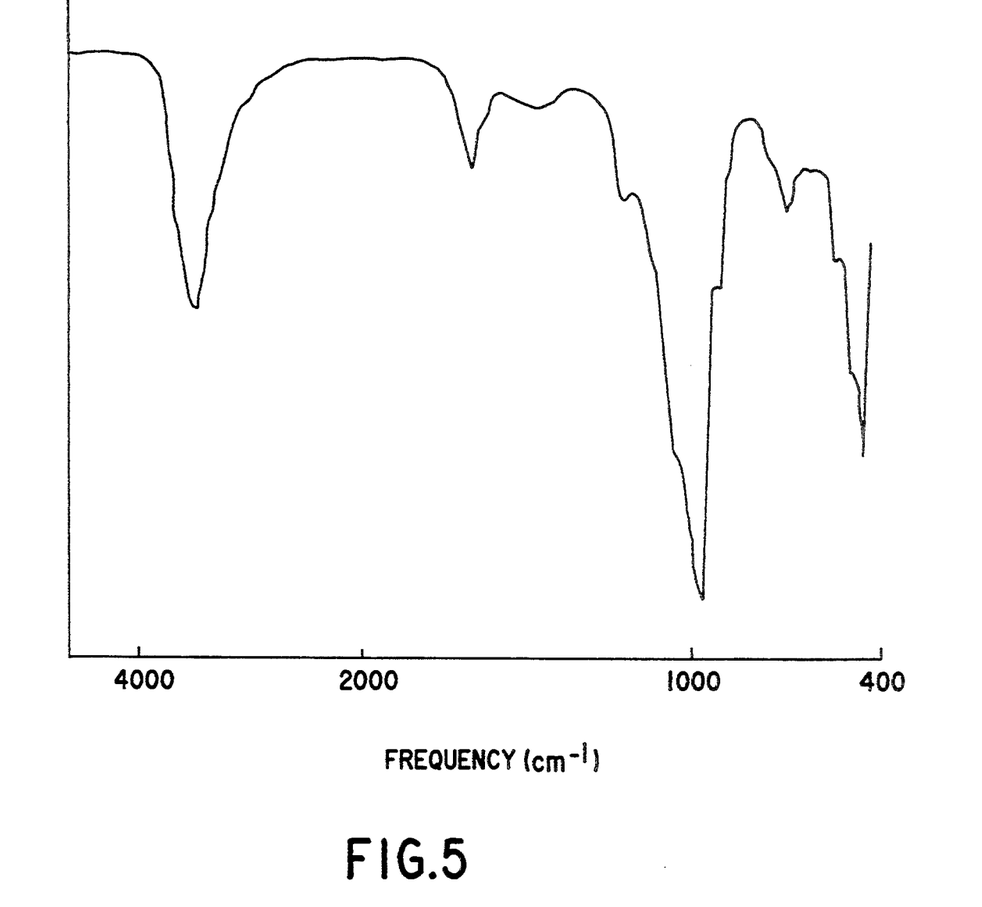
FIG. 5 is a graph showing an IR pattern of T1 to T5.
Figure 6:
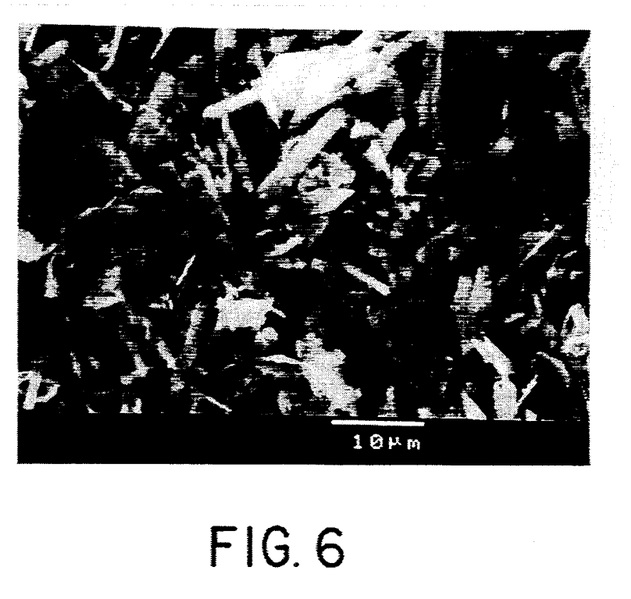
Figure 7:
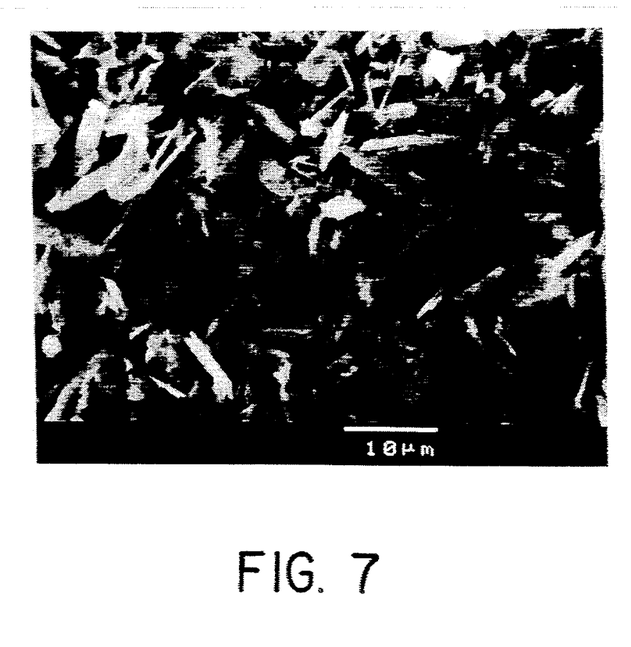
FIG. 7 is a graph showing an electron photomicrograph of T1 to T5.
Figure 8:
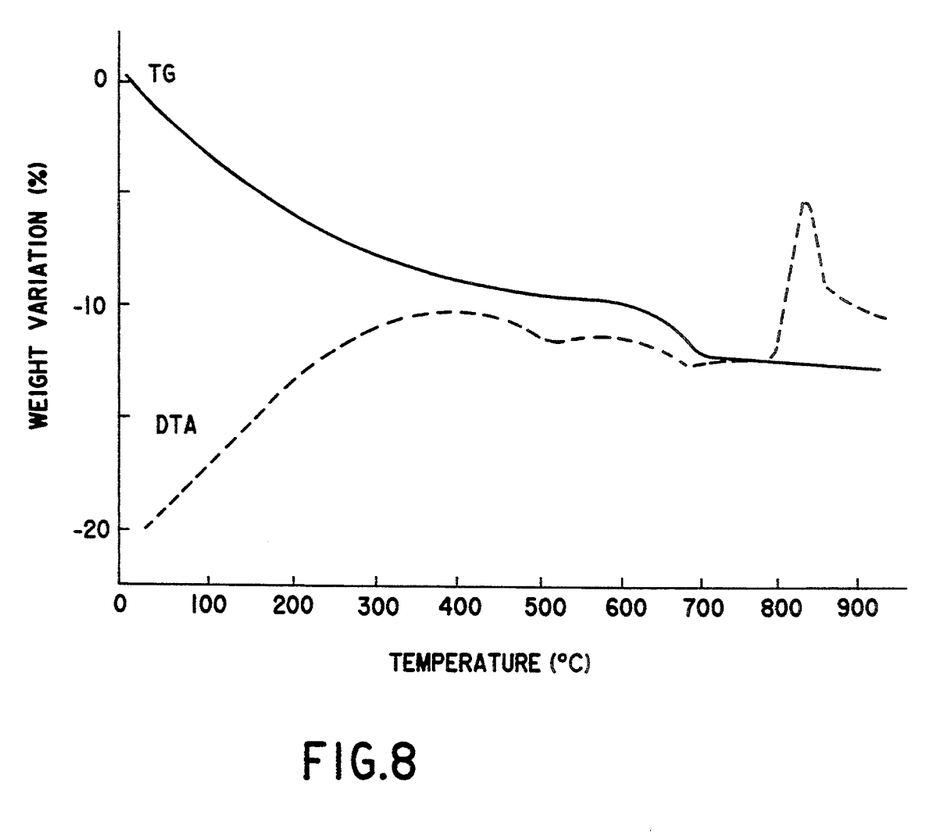
Figure 9:
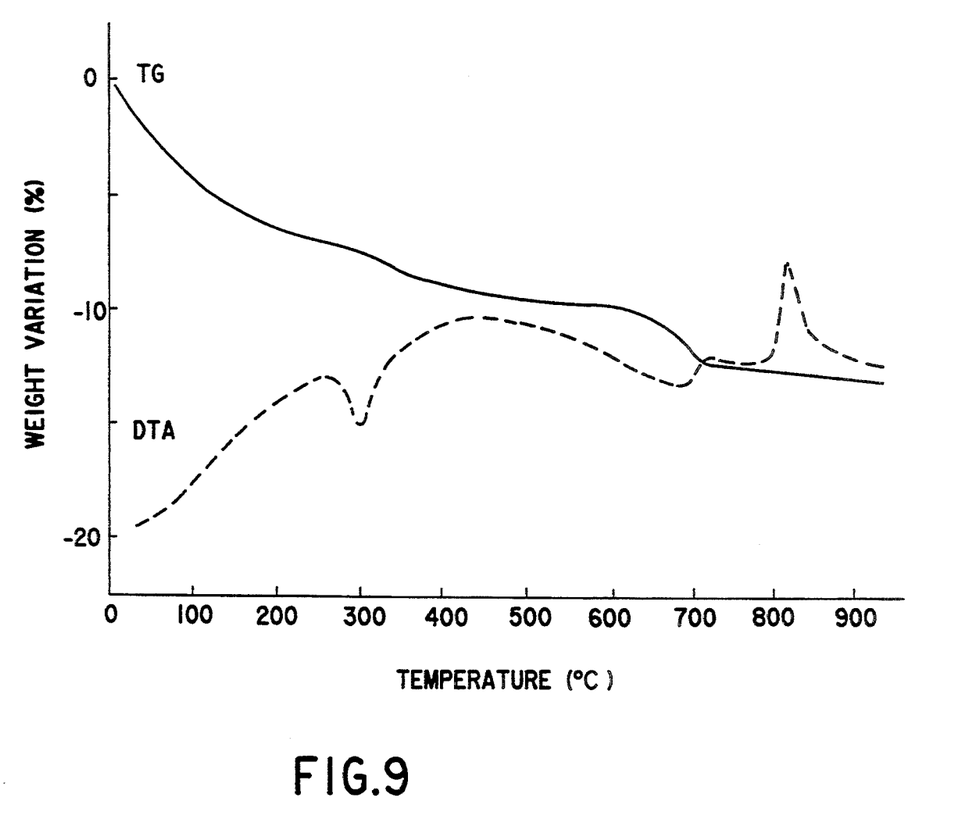
FIG. 9 is a graph showing TG-DTA curves of T1 to T5.

FIG. 4 shows an IR pattern of the tobermorite (TO), FIG. 5 that of the novel substances (T1-T5), FIG. 6 an electron photomicrograph of TO, FIG. 7 that of the novel substances (T1-T5), FIG. 8 TG-DTA curves of TO, and FIG. 9 those of the novel substances (T1-T5).

The powder X-ray diffraction pattern, IR patterns and electron photomicrographs revealed no difference between the tobermorite (TO) before the reaction and the novel substances (T1-T5). On the other hand, the TG-DTA curves showed a difference between the material and the novel substances in dehydration behavior at 150° to 550° C., especially at about 300° C., but the substances were found to be as excellent as the tobermorite (TO) before the reaction in heat resistance.

Example 2

To prepare an isotherm of ion exchange between $Ca^{2+}$ ions in the tobermorite (TO), the material for the novel substances of the invention, and silver ions in an aqueous solution based on the results of Example 1, 1.0 g of the dry fine tobermorite powder was admixed with 400 ml of each of aqueous silver nitrate solutions having varying concentrations of 1.0 to 64.0 mM, and was reacted therewith with stirring for 24 hours in a water bath having a constant temperature of 25° C. To prevent formation of carbonate, oxide and like by-products at this time, the solution was deaerated, and the air to be in contact with the solution was replaced by nitrogen. The concentrations of different cations in the aqueous solution were determined after the 24-hour reaction by the same methods as used in Example 1. Table 3 and FIG. 10 show the results.

TABLE 3

| Initial $Ag^+$ ion conc. (mmole/l) | 1.02 | 5.09 | 7.64 | 10.2 | 19.9 | 47.9 | 63.9 |
|---|---|---|---|---|---|---|---|
| Equilibrium $Ag^+$ ion conc. (mmol/l) | 0.30 | 2.37 | 4.05 | 5.95 | 13.0 | 40.9 | 56.9 |
| Conc. of $Ag^+$ ions removed (mmol/l) | 0.72 | 2.72 | 3.59 | 4.23 | 6.9 | 7.0 | 7.0 |
| Conc. of $Ca^{2+}$ ions released (mmol/l) | 0.37 | 1.30 | 1.77 | 2.10 | 3.4 | 3.4 | 3.4 |
| Conc. of $Na^+$ ions released (mmol/l) | 0.01 | 0.02 | 0.05 | 0.06 | 0.13 | 0.13 | 0.13 |
| Amount of $Ag^+$ ions removed (mmol/l) | 0.29 | 1.09 | 1.44 | 1.69 | 2.76 | 2.80 | 2.80 |

Figure 10:
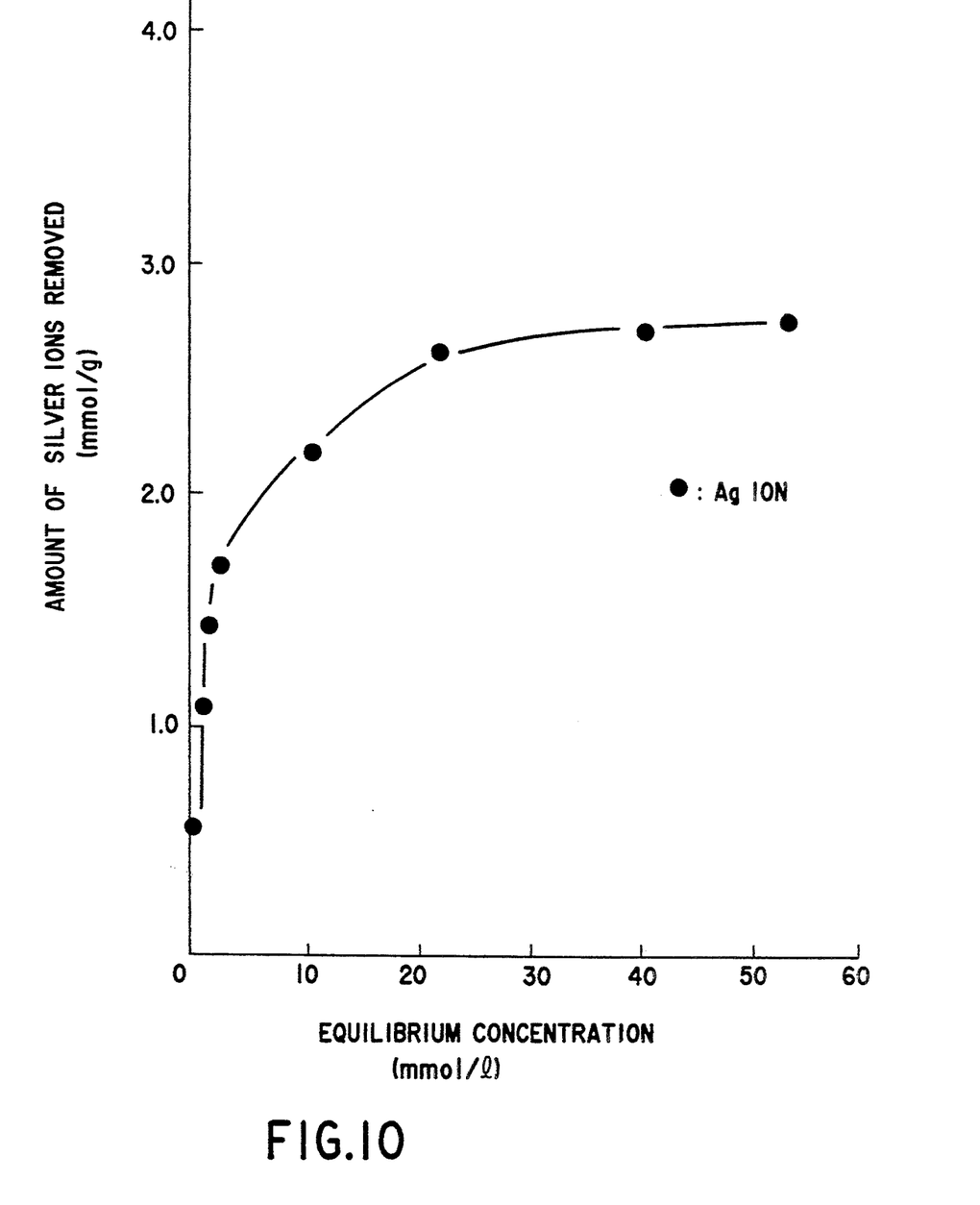
FIG. 10 is a graph showing an isotherm of cation exchange between TO and silver ions.

Table 3 and FIG. 10 reveal that although silver ions in the aqueous solution were incorporated into the tobermorite almost 100% when the concentration of silver nitrate solution was low, the ratio gradually decreased with an increase in the concentration, thus showing cation exchange characteristics of the Langmuir type.

The amount of silver incorporated into the interlayer spaces of the tobermorite increased with a rise in the concentration of silver nitrate solution but did not exceed a certain value when the silver nitrate solution used for the reaction was not lower than about 20.0 mM in concentration. This value was 2.80 mmoles/g, which is the amount of silver ions exchanged for 100% of the interlayer $Ca^{2+}$ ions and about 10% of $Na^+$ ions present in the interlayer spaces of 1.0 g of tobermorite crystals. This indicates that silver ions in the aqueous solution at 25° C. are exchangeable for the interlayer $Ca^{2+}$ ions of the tobermorite crystals 100% but are exchangeable for only 10% of the interlayer $Na^+$ ions thereof, and are not exchangeable for the interlayer $Ca^+$ ions in the layers forming the crystal lattice.

Example 3

Based on the results of Example 2, novel substances were prepared which were different in the amount of silver incorporated therein. More specifically, 25 g of TO was admixed with 10.0 liters of each of silver nitrate solutions having a concentration of 0.255 mM, 0.509 mM, 1.018 mM, 10.0 mM or 31.9 mM and was reacted therewith for cation exchange at room temperature with stirring. To prevent formation of carbonate, oxide and like by-products at this time, the solution was deaerated, and the air to be in contact with the solution was replaced by nitrogen. The reaction mixture was filtered by suction 24 hours later for solid-liquid separation. The solid portion was washed with distilled water and then dried in a vaccum at room temperature. In this way, novel substances were prepared. Table 4 shows the compositions, molecular weights, silver contents and specific surface areas of these substances. However, the calculation for the composition formulae was done neglecting the amount of silver ions exchanged for $Na^+$ ions because it was very small. The novel substances were hereinafter referred to as T1, T2, T3, T4, and T5 in the order of increasing silver content.

TABLE 4

| Sample | Composition (molecular weight) | Ag content | Specific surface area (m²/g) |
|---|---|---|---|
| $T_1$ | $Ca_{4.99}Ag_{0.03}Na_{0.39}H_{0.16}$—$(Si_{5.45}Al_{0.55}O_{18}H_2).4H_2O$ = 742.26 | 0.04 mmol/g | 57.0 m²/g |
| $T_2$ | $Ca_{4.97}Ag_{0.07}Na_{0.39}H_{0.16}$—$(Si_{5.45}Al_{0.55}O_{18}H_2).4H_2O$ = 745.77 | 0.09 mmol/g | 55.7 m²/g |
| $T_3$ | $Ca_{4.93}Ag_{0.14}Na_{0.39}H_{0.16}$—$(Si_{5.45}Al_{0.55}O_{18}H_2).4H_2O$ = 751.71 | 0.19 mmole/g | 53.9 m²/g |
| $T_4$ | $Ca_{4.40}Ag_{1.20}Na_{0.39}H_{0.16}$—$(Si_{5.45}Al_{0.55}O_{18}H_2).4H_2O$ = 844.81 | 1.44 mmol/g | 51.5 m²/g |
| $T_5$ | $Ca_{4.00}Ag_{2.00}Na_{0.39}H_{0.16}$—$(Si_{5.45}Al_{0.55}O_{18}H_2).4H_2O$ = 915.08 | 2.21 mmol/g | 40.3 m²/g |

Experimental Example 1

To test the novel substances of the invention, T1, T2, T3, T4, and T5, listed in Table 4 and the silver-free tobermorite T0 for ethylene gas adsorbing ability, each of T0 to T5 was dried in a vacuum at 60° C. for 5 hours, 1.0 g of the dried substance was weighed out and placed into a bag of nonwoven fabric (lined with a polyethylene laminate inside), and the bag was heat-sealed for use as a sample for adsorbing ethylene gas.

Figure 11:
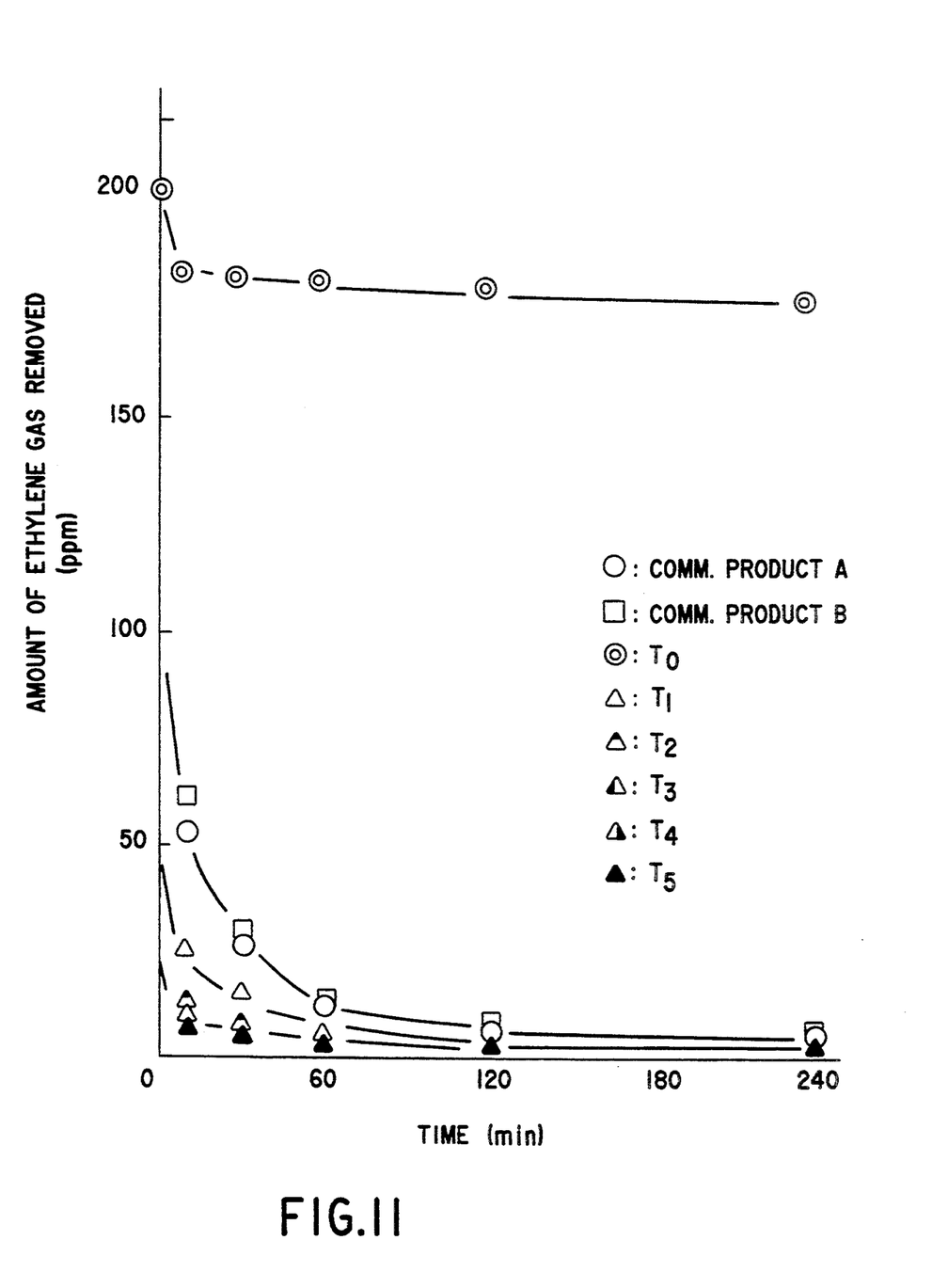
FIG. 11 is a graph showing the ethylene adsorbing ability of TO and T1 to T5.

For an ethylene gas adsorption experiment, the ethylene gas adsorbing sample thus prepared was placed into a resin container, the air therein was replaced by an ethylene gas having a concentration of 203 ppm (in $N_2$ gas), immediately followed by measurement of time, and the ethylene gas concentration was determined by gas chromatography at a predetermined time interval. FIG. 11 shows the results. The commercial products A and B are aforementioned silver-incorporating zeolites.

FIG. 11 reveals that T1, T2, T3, T4 and T5 exhibited higher ethylene gas adsorbing ability than the commercial products A and B. Although the adsorption rate decreases in the order of decreasing silver content, i.e., in the order of T1, T2, T3, T4 and T5, the ethylene adsorbing ability of each substance is concenquently fully satisfactory. Thus, the present substances are expected to have an effect for use as freshness maintaining agents of the ethylene adsorbing type. On the other hand, the tobermorite containing no silver exhibited only 20% of the ethylene adsorbing ability of T1, T2, T3, T4 and T5 and the commercial products A, B and was found almost ineffective as an ethylene-adsorbing freshness maintaining agent.

Experimental Example 2

To test the novel substances of the invention, T1, T2, T3, T4 and T5, listed in Table 4 and the silver-free tobermorite (T0) for antibacterial properties, 100 mg of each of these substances was dispersed in 1.0 ml of distilled water, and paper disks, 30 mm in diameter, were impregnated with the dispersion and dried to prepare test disks, whereby each of the disl was caused to support several to several tens of milligrams of the novel substance thereon. *Escherichia coli* and *Staphylococcus aureus* were used as a culture medium. The antibacterial test was conducted by the disk method. More specifically, the medium was prepared in a dish, 90 mm in diameter, innoculated with 0.1 ml of physiological saline having $10^8$ cells/ml of each strain of bacteria suspended therein and thereafter spreaded with a glass spreader, and the test disk was affixed to the resulting medium. The dish was thereafter maintained. at 37° C. for 18 hours for incubation, and the culture was checked for formation of an inhibition zone. Table 5 shows the results. The symbol + indicates formation of inhibition zone, and the symbol − absence of the zone.

TABLE 5

| Bacterium | Substance contained in disk | | | | | | |
|---|---|---|---|---|---|---|---|
|  | None | T0 | T1 | T2 | T3 | T4 | T5 |
| *Escherichia Coli* | − | − | + | + | + | + | + |
| *Staphylococcus aureus* | − | − | + | + | + | + | + |

Table 5 shows that the growth of the bacteria on the media having affixed thereto the disk containing the novel substance T1, T2, T3, T4 or T5 was apparently inhibited unlike the medium carrying no disk or having the disk containing T0. Thus, the novel substances T1, T2, T3, T4 and T5 were found to have satisfactory antibacterial properties.

Experimental Example 3

The novel substances of the invention, T1, T2, T3, T4 and T5, listed in Table 4 and the silver-free tobermorite (T0) were tested on bacteria to determine mortality by the shaking flask method. More specifically, $1.26 \times 10^6$ or $1.21 \times 10^6$ cells/ml of *Escherichia coli* or *Staphylococcus aureus* were suspended in 60 ml of 0.05M phosphate buffer (pH 7.0), 10 mg of dry powder of the present novel substance T1, T2, T3, T4 or T5 was admixed with the suspension, and the mixture was shaken at 30° C. for 1 hour at 130 r.p.m. One hour later, the mixture was sampled and diluted, and Muller Hinton medium was innoculated with the dilution, followed by incubation at 30° C. for 1 week. The number of colonies on each of the cultures thus prepared was counted to calculate the mortality. Further each mixture resulting from the one-hour shaking procedure was checked by the atomic absorption method for the amount of silver dissolving out into the mixture. Table 6 shows the results.

TABLE 6

| Bacterium | Substance | 0 hr | 1 hr | Mortality (%) | Ag ions dissolving out (ppb) |
|---|---|---|---|---|---|
| Escherichia coli | None | $1.26 \times 10^6$ | $1.14 \times 10^6$ | 9.5 | — |
| | $T_0$ | | $1.11 \times 10^6$ | 11.9 | — |
| | $T_1$ | | <10 | 100 | N.D |
| | $T_2$ | | <10 | 100 | 1 |
| | $T_3$ | | <10 | 100 | 2 |
| | $T_4$ | | <10 | 100 | 7 |
| | $T_5$ | | <10 | 100 | 9 |
| Staphylococcus aureus | None | $1.21 \times 10^6$ | $1.10 \times 10^6$ | 7.9 | — |
| | $T_0$ | | $1.08 \times 10^6$ | 10.7 | — |
| | $T_1$ | | <10 | 100 | N.D |
| | $T_2$ | | <10 | 100 | 1 |
| | $T_3$ | | <10 | 100 | 2 |
| | $T_4$ | | <10 | 100 | 7 |
| | $T_5$ | | <10 | 100 | 9 |

Table 6 reveals that nearly all bacteria were found alive in the suspensions containing the cells only or in the suspensions containing TO, further showing that the bacteria were almost completely killed in the suspensions containing the novel substance T1, T2, T3, T4 or T5 and were not detectable.

Examples 2 and 3 demonstrate that the novel substances of the present invention, T1, T2, T3, T4 and T5, exhibit outstanding antibacterial properties, permit only a trace of silver to dissolve out and are therefore expected to be usable as antibacterial agents which are safe to the human body.

Industrial Applicability

The silver-containing tobermorite of the present invention is excellent in heat resistance, water resistance and mechanical strength, further has ethylene-adsorbing ability and antibacterial properties, and is therefore effectively usable not only in the fields in which conventional tobermorites are utilized but also as an agent for maintaining freshness of vegetables and fruits and antibacterial agent for various substances.

We claim:

1. A silver-containing tobermorite having a composition of $Ca_{5-y/2}Ag_{y+z}M_{x-z}(Si_{6-x}Al_xO_{18}H_2) \cdot 4H_2O$, where $0 \leq x \leq 1$, $0.001 \leq y \leq 2$, $0 \leq z \leq 0.1$, M is a monovalent cation, prepared from a tobermorite having the composition $Ca_5M_x(Si_{6-x}Al_xO_{18}H_2) \cdot 4H_2O$, where $0 \leq x \leq 1$, M is a monovalent cation as defined above, by exchanging silver ion for the interlayer cation $Ca^{2+}$, or both $Ca^{2+}$ and monovalent cation $M^+$ of the tobermorite.

* * * * *